United States Patent [19]

Jacobus et al.

[11] Patent Number: 5,972,904
[45] Date of Patent: Oct. 26, 1999

[54] METHOD OF TREATING SINUSITIS WITH URIDINE TRIPHOSPHATES AND RELATED COMPOUNDS

[75] Inventors: Karla Jacobus, Cary; Janet Rideout; Ben Yerxa, both of Raleigh; William Pendergast, Durham; Suhaib Siddiqi, Raleigh, all of N.C.; David Drutz, Houston, Tex.

[73] Assignee: Inspire Pharmaceuticals, Inc., Durham, N.C.

[21] Appl. No.: 09/004,786

[22] Filed: Jan. 9, 1998

Related U.S. Application Data

[62] Division of application No. 08/675,620, Jul. 3, 1996, Pat. No. 5,789,391.

[51] Int. Cl.$^6$ ................................................. A61K 31/70
[52] U.S. Cl. ........................ 514/51; 514/47; 424/45; 424/46
[58] Field of Search .................... 514/47, 51; 424/45, 424/46

[56] References Cited

U.S. PATENT DOCUMENTS

| | | |
|---|---|---|
| 5,292,498 | 3/1994 | Boucher, Jr. . |
| 5,420,116 | 5/1995 | Puchelle et al. . |
| 5,635,160 | 6/1997 | Sutts et al. ................................ 424/45 |

FOREIGN PATENT DOCUMENTS

| | | |
|---|---|---|
| 2684299 | 12/1911 | France . |
| 2677250 | 6/1991 | France . |
| WO9211016 | 7/1992 | WIPO . |

OTHER PUBLICATIONS

Benali et al. "Effect of extracellular ATP and UTP . . . " Medline 94183573, 1994.
Zeiger "Propspects for ancillary treatment of sinusitis . . . " Medline 92407246, 1992.
Scrip 2067 Inspire pharmaceuticals focuses on chronis obstructive . . . , 1995.
Scrip 2151 US orphan status for Inspire's . . . , 1995.
Moss, A. and V. Parsons, 1985, National Center for Health Statistics, 1986, 66–7, DHHS Publication No. (PHS)89–1588.
Revonta, M. and A. Blokmanis, 1994, *Can Fam Physician*40, 1969–72, 1975–76.
Kennedy, D. 1990, *Otolaryngol. Head Neck Surg.* 103:845–846.
Reuler, J., 1995, *West J. Med.*: 40–8.
Boucher, R. et al., "Mechanisms and Therapeutic Actions of Uridine Triphosphates in the Lung." *Adenosine and Adenine Nucleotides From Molecular Biology to Integrative Physiology.*, pp. 525–553 L. Belardinelli, et al., Alumwer Academic.
Gheber, L. et al., 1995, *J. Membrane Biol.*147: 83–93.
Gobran. L. et al., 1994, *Am J. Physiol.* 267:L625–L633.
Cusack., N. and Hourani, S. "Biological Actions of Extracellular ATP" *Annals N.Y Acad. Sci.* pp. 525–553, (1990).
Hall and Khorana, 1954, J. Am. Chem. Soc. 76:5056.
Merck Index, Monograph No. 9795 (11$^{th}$ edition 1989).
Goody, R.S. and Eckstein, F.1971, *J. Am. Chem. Soc.* 93:6252.
Kenner et al., 1954, *J. Chem Soc.* 2288.
Rapaport, E. et al., 1981 *Proc. Natl. Acad. Sci. USA* 78(2): 838–842.
Ng, K. and Orgel, L.E. 1987, *Nucleic Acids Research*15(8):3572–80.
Hoard D. and Ott D. 1965, *J. Am. Chem Soc* 87:1785–1788.
Moffatt, J. and Khorana H. 1961, *J Am. Chem. Soc.* 649–659.
Fischer, B. et al., 1993, *J. Med. Chem.* 36:3937–3946.
Kotchtkov, N. et al., 1991 *Tetrahedron Lett* 1993.
Barrio, J. et al., 1972, *Biochem. Biophys. Res. Commun.* 46:397.
Secrist, J. et al., 1972, *Biochemistry* 11:3499.
Bierndt, J. et al., 1978, *Nucleic Acids Res.*5:789.
Koyasuga–Mikado, K. et al., 1980, *Chem. Pharm. Bull* . (Tokyo) 28:932.
Ludwig, J. and Eckstein, F. 1989, *J. Org. Chem.* 54, 631–635.
Blackburn, G. et al., 1984, *J. Chem. Soc.* Perkin Trans. 1:1119:1125.
Eckstein,F. and Goody, R. 1963, *Biochemistry* 15:1685.
Myers, T. et al. 1963, *J. Am. Chem. Soc.* 85:3292–3295.
Benali et al., 1994 "Effects of Extracellular ATP and UTP . . . " Medline 94183573.
Zeiger 1992 "Prospects for ancillary treatment of sinusitis . . . " Medline 92407246.
Scrip 1995 2067 Inspire Pharmaceuticals focuses on chronic obstructive . . .
Scrip 1995 2151 US orphan status for Inspire's . . .
Am. Aca. Allerge and Immunology "sinusitis" Pamphlet 1993.
Kintaka et al. "Analysis of small airway dysfunction in chronic sinusitis" BA 94:045430 1992.

*Primary Examiner*—Ceila Chang
*Attorney, Agent, or Firm*—Albert P. Halluin; John A. Bendrick; Howrey & Simon

[57] ABSTRACT

A method of promoting drainage of congested mucous secretions in the sinuses of a subject in need of such treatment is disclosed. The method comprises administering to the sinuses of the subject a uridine phosphate such as uridine 5'-triphosphate (UTP) or $P^1,P^4$-di(uridine-5') tetraphosphate ($U_2P_4$), an analog of UTP, or any other analog, in an amount effective to promote drainage of congested fluid in the sinuses by hydrating mucous secretions or by stimulating ciliary beat frequency in the sinuses. Pharmaceutical formulations and methods of making the same are also disclosed. Methods of administering the same would include any liquid suspension (including nasal drops or spray), oral form (liquid or pill), aerosol inhalation, powder form, topical, injected, intra-operative instillation or suppository form.

13 Claims, No Drawings

METHOD OF TREATING SINUSITIS WITH URIDINE TRIPHOSPHATES AND RELATED COMPOUNDS

This application is a divisional of application Ser. No. 08/650,620, filed Jul. 03, 1996, now U.S. Pat. No. 5,789,391, the disclosure of which is incorporated herein by reference.

TECHNICAL FIELD

This invention relates to a method of removing or preventing the accumulation of retained mucous secretions from the sinus passages of a patient by admninistering certain uridine, adenosine, or cytidine triphosphates.

BACKGROUND OF THE INVENTION

Sinusitis is an inflammation of the paranasal sinuses typically Associated with an upper respiratory infection. Sinusitis is this country's most common health-care complaint, affecting an estimated 31 million people. (A. Moss and V. Parsons, National Center for Health Statistics, 1986: 66-7, DHHS Publication No. (PHS)86-1588 (1985)). Other less common causes include allergies, air pollution, diving and swimming under water, structural defects of the nose (deviated septum), and as a complication of dental work. A common complication of sinusitis is a related middle ear infection (otitis media) due to the close proximity of the sinuses and eustachian tube. (M. Revonta and A. Blokmanis, *Can. Fam. Physician* 40, 1969–72, 1975–76 (1994)). In addition, most patients with primary ciliary diskinesia experience chronic or recurrent episodes of sinusitis.

As the sinus inflammation progresses, mucus from the sinuses becomes trapped within the sinus passages. This blockage of mucus contributes to the headache, pain, fever, and difficulty in breathing commonly reported in this disorder. Common symptoms are headache, tenderness or discomfort over the forehead and sinus area of the face, nasal discharge, slight increase in temperature, and general malaise.

At the present time, current treatment for sinusitis consists of antibiotics for the infection, antihistamine/decongestant agents (typically nasal spray or drops) or saline nasal sprays to relieve congestion, mucolytic agents, steam inhalation, warm compresses applied over the sinus area, analgesics, and anti-inflammatory agents to relieve discomfort. (D. Kennedy, *Otolaryngol. Head Neck Surg.* 103, 845–46 (1990)). In addition, exposure to environmental irritants, such as pollution, smoke, and dust should be eliminated or reduced. If the sinusitis becomes a chronic problem, surgical enlargement and drainage of the sinus passages may be considered.

An additional patient population at risk for development of sinusitis is patients who are intubated with a nasotracheal tube. (J. Reuler, *West J. Med.* 163(1), 40–8 (1995)). The tube irritates the lining of the nasopharyngeal airways, and because of the close proximity to the sinuses and the large number of microorganisms present in the nasopharyngeal airways, severe sinusitis may result. At present, treatment measures remain similar to those described above, induding antibiotics, analgesics, warm compresses, and surgical drainage, but also require removal of the nasotracheal tube and reintubation by tracheostomy, or, in fewer cases, by the oropharyngeal route. The symptoms of this type of sinusitis are intense discomfort and tenderness over the sinus area, increased drainage from the naso-sinus airways, fever, and potentially other, more severe infections and complications.

Uridine 5'-triphosphate (UTP) and adenosine 5'-triphosphate (ATP) have been shown to affect the ion transport activity of human airway epithelial cells, as described in U.S. Pat. No. 5,292,498. Specifically, UTP and ATP induce chloride and water secretion in the lung epithelial cells of cystic fibrosis patients, helping to liquify and facilitate transport of the highly viscous airway surface mucus that characterizes this disease. It has also been found that UTP and ATP stimulate the ciliary beat frequency in lung epithelial cells, further facilitating the transport of mucus from the lungs of cystic fibrosis patients, pneumonia patients, or normal individuals. (R. Boucher, et al., Adenosine and Adenine Nudeotides: From Molecular Biology to Integrative Physiology, p. 525–32 entitled "Mechanisms and Therapeutic Actions of Uridine Triphosphates in the Lung" (L. Belardinelli, et al. ed., Alumwer Academic Publishers, Boston 1995); (L. Gheber, et al. *J. Membrane Biol.* 147, 83–93 (1995)). A French biotechnology company, Laboratoires SYNTHELABO FRANCE, has developed a method of treating nasal mucous fluid congestion under the trademark name rhinATP™ which uses adenosine triphosphate (ATP) as the active compound. This technology for rhinATP™ was licensed under U.S. Pat. No. 5,420,116 (applicant intends the disclosure of this and all other patent references and publications cited herein be incorporated herein by reference). Their method of treatment comprises administering ATP to the nasal cavity via nasal spray or nasal drops.

Applicant has discovered that the clearance of the retained mucous fluid in sinusitis patients can be facilitated by administering UTP and its related compounds as well as other nucleoside phosphates such as: $P^1,P^4$-di(uridine-5') tetraphosphate ($U_2P_4$); adenosine 5'-triphosphate (ATP); cytidine 5'-triphosphate (CTP); 1,$N^6$-ethenoadenosine 5'-triphosphate; adenosine 1-oxide 5'-triphosphate; 3,$N^4$-ethenocytidine 5'-triphosphate; or $P^1,P^4$-di(adenosine-5') tetraphosphate ($A_2P_4$) to the site of fluid blockage. UTP and $U_2P_4$ are the preferred embodiments of the present invention. By administering UTP or $U_2P_4$ soon after symptoms first appear, total blockage of the sinuses and the resulting symptoms may be avoided.

SUMMARY OF THE INVENTION

A method of treating sinusitis in a subject in need of such treatment is disdosed. The method comprises administering to the patient a compound of Formula I, or a pharmaceutically acceptable salt thereof, in an amount effective to hydrate mucous secretions and stimulate ciliary beat frequency in the lurninal epithelial cells of the sinus passages:

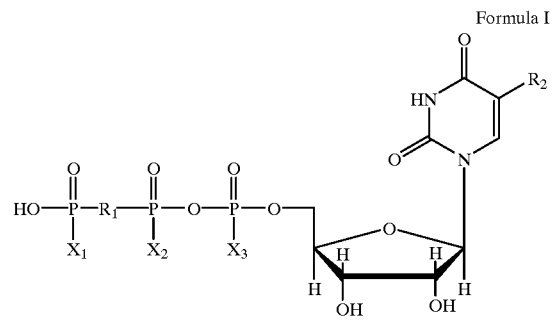

Formula I wherein:

$X_1$, $X_2$, and $X_3$ are each independently either $O^-$ or $S^-$. Preferably, $X_2$ and $X_3$ are $O^-$.

$R_1$ is O, imido, methylene, or dihalomethylene (e.g., dichloromethylene, diflouromethylene). Preferably, $R_1$ is oxygen or difluoromethylene.

$R_2$ is H or Br. Preferably, $R_2$ is H. Particularly preferred compounds of Formula I are uridine 5'-triphosphate [ULTP] and uridine 5'-(3thiotriphosphate) [UTPγS].

In addition to Formula I, Formula II-$P^1,P^4$ di(uridine-5') tetraphosphate [$U_2P_4$] is also a preferred embodiment of the invention. Another compound of Formula II is $P^1,P^4$-di (adenosine-5') tetraphosphate [$A_2P_4$]. The method of the present invention can also include administering a compound of Formula III (adenosine 5'-triphosphate [ATP] or 1,$N^6$-ethenoadenosine 5'-triphosphate or adenosine 1-oxide 5'-triphosphate), or Formula IV (cytidine 5'-triphosphate [CTP] or 3,$N^4$-ethenocytidine 5'-triphosphate).

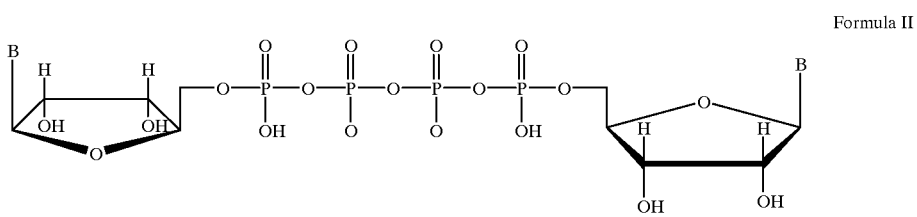

Formula II wherein:

B is uracil or adenine, attached as shown in Formulae I and III.

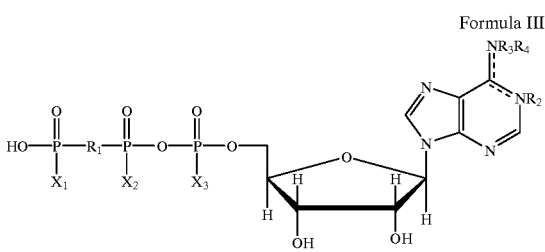

Formula III

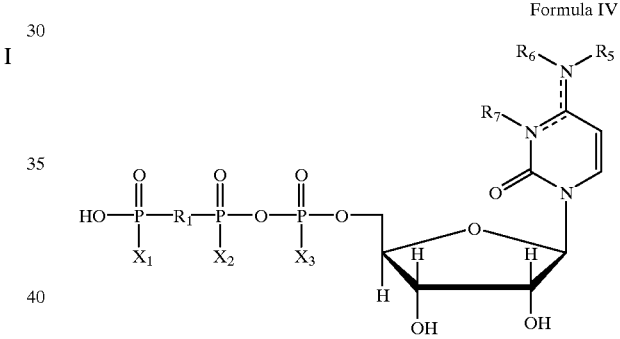

Formula IV wherein:

$R_1$, $X_1$, $X_2$, and $X_3$ are defined as in Formula I.

$R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$ and $R_2$ taken together are —CH=CH—, forming a ring from N-6 to N-1 with a double bond between N-6 and C-6 (1,$N^6$-ethenoadenine).

wherein:

$R_1$, $X_1$, $X_2$, and $X_3$ are defined as in Formula I.

$R_5$ and $R_6$ are H while $R_7$ is nothing and there is a double bond between N-3 and C-4 (cytosine), or, $R_5$, $R_6$ and $R_7$ taken together are —CH=CH—, forming a ring from N-3 to N-4 with a double bond between N-4 and C-4 (3,$N^4$-ethenocytosine).

A second aspect of the present invention is a pharmaceutical formulation containing the compound of Formula I, II, III, or IV in an amount effective to hydrate mucous secretions and stimulate ciliary beat frequency in the luminal epithelial cells of the sinus passages in a patient in need of such treatment.

A third aspect of the present invention is the use of the active compounds disclosed herein for the manufacture of a medicament for the therapeutic hydration of mucous secretions and stimulation of ciliary beat frequency in the luminal epithelial cells of the sinus passages in a patient in need of such treatment.

DESCRIPTION OF THE SPECIFIC EMBODIMENTS

The method of the present invention may be used to hydrate retained mucous secretions and stimulate ciliary beat frequency in the sinuses of a subject in need of such treatment. The present invention increases mucociliary clearance in three ways: (1) by increasing the ciliary beat frequency of cilia on the surface of luminal epithelia cells, (2) by increasing the secretions of mucins by goblet cells, and (3) by increasing the secretion of water into the periciliary liquid layer as a result of increased secretion of Cl⁻ ions by luminal epithelial cells. In addition, data suggests that UTP increases surfactant phospholipid production and secretion by type II aveolar cells in vitro. (L. Gobran, et al., *Am. J. Physiol.* 267, L625–L633 (1994)). The mucins secreted by goblet cells form a layer on top of the cilia and capture foreign particles, including viruses and bacteria; the mucin layer is transported by the wave-like action of cilia; and the movement of cilia is facilitated by the hydration of the periciliary liquid layer surrounding the cilia.

The present invention is concerned primarily with the treatment of human subjects, but may also be employed for the treatment of other mammalian subjects, such as dogs and cats, for veterinary purposes.

Compounds illustrative of the compounds of Formula I above include: (a) uridine 5'-triphosphate (UTP); (b) uridine 5'-O-(3-thiotriphosphate) (UTPγS); and (c) 5-bromo-uridine 5'-triphosphate (5BrUTP). These compounds are known or may be made in accordance with known procedures, or variations thereof which will be apparent to those skilled in the art. See generally N. Cusack and S. Hourani, *Annals N.Y. Acad. Sci.* 603, 172–81 (entitled "Biological Actions of Extracellular ATP"). For example, UTP may be made in the manner described in Kenner, et al., *J. Chem. Soc.* 1954, 2288; or Hall and Khorana, *J. Am. Chem. Soc.* 76, 5056 (1954). See Merck Index, Monograph No. 9795 (11th Ed. 1989). UTPγS may be made in the manner described in R. S. Goody and F. Eckstein, *J. Am. Chem. Soc.* 93, 6252 (1971).

For simplicity, Formulae I-IV herein illustrate the active compounds in the naturally occuring D-configuration, but the present invention also encompasses compounds in the L-configuration, and mixtures of compounds in the D- and L-configurations, unless otherwise specified. The naturally occuring D-configuration is preferred.

Compounds illustrative of the compounds of Formula II include (P¹,P⁴-di(adenosine-5') tetraphosphate (A₂P₄) or P¹,P⁴-di(uridine-5') tetraphosphate (U₂P₄). These compounds can be made in accordance with known procedures, or variations thereof which will be described by: P. Zamecnik, et al., *Proc. Natl. Acad. Sci. USA* 89, 838–42 (1981); and K. Ng and L. E. Orgel, *Nucleic Acids Res.* 15 (8), 3572–80 (1987). U₂P₄ can be prepared by methods similar to that described in C. Vallejo, et al., *Biochem. Biophys. Acta* 438,304–09 (1976).

Compounds illustrative of the compounds of Formula III above include (a) adenosine 5'-triphosphate (ATP) and (b) 1,N⁶-ethenoadenosine 5'-triphosphate. Compounds illustrative of the compounds of Formula IV above include (a) cytidine 5'-triphosphate and (b) 3,N⁴-ethenocytidine 5'-triphosphate. These compounds can be made in accordance with known procedures, or variations thereof which will be apparent to those skilled in the art. For example, phosphorylation of nucleosides by standard methods such as D. Hoard and D. Ott, *J. Am. Chem. Soc.* 87, 1785–1788 (1965); M. Yoshikawa, et al., *Tetrahedron Lett.* 5065–68 (1967) and *idem., Bull. Chem. Soc.* (Jpn) 42, 3505–08 (1969); J. Moffatt and H. Khorana, *J. Am. Chem. Soc.* 83, 649–59 (1961); and B. Fischer, et al., *J. Med. Chem.* 36, 3937–46 (1993) and references therein. Etheno derivatives of cytidine and adenosine are prepared by known methods such as: N. Kotchetkov, et al., *Tetrahedron Lett.* 1993 (1971); J. Barrio, et al., *Biochem. Biophys. Res. Commun.* 46, 597 (1972); J. Secrist, et al., *Biochemistry* 11, 3499 (1972); J. Bierndt, et al., *Nucleic Acids Res.* 5, 789 (1978); K. Koyasuga-Mikado, et al., *Chem. Pharm. Bull. (Tokyo)* 28, 932 (1980). Derivatives with alpha, beta and gamma thiophosphorus groups can be derived by the following or by adapting methods of: J. Ludwig and F. Eckstein, *J. Org. Chem.* 54, 631–35 (1989); F. Eckstein and R Goody, *Biochemistry* 15, 1685 (1976); R. Goody and F. Eckstein, *J. Am. Chem. Soc.* 93, 6252 (1971).

Compounds of Formulas I, III, or IV where $R_1$ is $CCl_2$ and $CF_2$ can be prepared by methods similar to that described in G. Blackburn, et al., *J. Chem. Soc. Perkin Trans.* I, 1119–25 (1984). Compounds of Formula I, II, III where $R_1$ is $CH_2$ can be prepared by methods similar to that described in T. Myers, et al., *J. Am. Chem. Soc.* 85, 3292–95 (1963).

In addition, UTP, ATP, CTP, $A_2P_4$, 3,N⁴-ethenocytidine triphosphate, 1,N⁶-ethenoadenine 5'-triphosphate, adenosine 1-oxide 5'-triphosphate, ATPγS, ATPβS, ATPαS, AMPPCH₂P, AMPPNHP, N⁴-ethenocytidine and 1,N⁶-ethenoadenosine are commercially available, for example, from Sigma Chemical Company, PO Box 14508, St. Louis, Mo. 63178.

The active compounds of Formulae I–IV may be administered by themselves or in the form of their pharmaceutically acceptable salts, e.g., an alkali metal salt such as sodium or potassium, an alkaline earth metal salts, or an ammonium and tetraalkyl ammonium salts, $NX_4^+$ (wherein X is $C_{1-4}$). Pharmaceutically acceptable salts are salts that retain the desired biological activity of the parent compound and do not impart undesired toxicological effects.

The active compounds disclosed herein may be administered to the lungs, sinuses, ears or eyes by a variety of suitable means, but are preferably administered by administering a liquid/liquid suspension (either a nasal spray of respirable particles which the subject inhales, or nasal drops of a liquid formulation, or eye drops of a liquid formulation) comprised of the active compound. Liquid pharmaceutical compositions of the active compound for producing a nasal spray or nasal powder, or nasal or eye drops may be prepared by combining the active compound with a suitable vehicle, such as sterile pyrogen free water or sterile saline by techniques known to those skilled in the art.

The dosage of active compound to hydrate mucous secretions and stimulate ciliary beat frequency in the sinuses will vary depending on the state of the subject, but generally an effective amount is the amount sufficient to achieve concentrations of active compound on the sinus passages of the subject of from about $10^{-7}$ moles/liter (e.g., for UTP, 0.0001 mg/mL) to about $10^{-1}$ moles/liter (e.g., for UTP, 52 mg/mL), and more preferably from about $10^{-6}$ moles/liter (e.g., for UTP, 0.001 mg/mL) to about $10^{-1}$ moles/liter (e.g., for UTP, 50 mg/mL).

Depending upon the solubility of the particular formulation of active compound administered, the daily dose to promote fluid drainage may be divided among one or several unit dose administrations. Preferably, the daily dose schedule is no more than four times per day.

Another means of administering the active compound to the sinuses of the patient to promote fluid/secretion drainage may include any oral form of the active compound, administered to the patient either by means of a liquid suspension of the active compound which is poured into the mouth of the patient, or by means of a pill form swallowed by the patient.

Another means of administering an effective amount of the active compound to the sinuses would involve administering a nebulized form of the active compound into the respiratory tract, such that the active compound enters the nasopharnyx and lungs and reaches the sinuses either directly or via systemic absorption and circulation. The active compound can be aerosolized in a variety of forms, such as, but not limited to, dry powder inhalants, metered dose inhalants, or liquid/liquid suspensions. In dry powder delivery, the UTP may be formulated alone or in combination with diluent or carrier, such as sugars (i.e., lactose, sucrose, trehalose, mannitol) or other acceptable excipients for lung or airway delivery. The dry powder may be obtained by methods known in the art, such as spray-drying, milling, freeze-drying, etc.

Another means of administering the active compound to the sinuses would include any topical form of the active compound, administered as a cream or gel to the nose, eyes or outer ear, which would subsequently permeate into the sinus passages of the patient.

Another means of administering the active compound to the sinuses would involve an injected form of the active compound, injected from the nose or sinus area of the face directly into the sinus passageways.

Another means of administering the active compound to the sinuses would involve a suppository form of the active compound, such that a therapeutically effective amount of the compound reaches the sinuses via systemic absorption and circulation.

Another means of administering the active compound would involve intra-operative instillation of a gel, cream, powder, foam, crystal or liquid suspension form of the active compound such that a therapeutically effective amount reaches the sinuses.

The preferred embodiments of the present invention-UTP and $U_2P_4$, as well as the other compounds for Formulae I–IV also have therapeutic benefit when used in combination with other agents used to treat sinusitis, such as, but not limited to: antibiotics; antiviral agents; antihistamine/decongestant agents; steam inhalation; mucolytic agents; nonsteroidal antiinflammatory agents; steroids; and warm compresses applied over the sinus area of the face.

The present invention is explained in greater detail in the Example which follows. This example is intended as illustrative of the invention, and is not to be taken as limiting thereof.

EXPERIMENTAL

EXAMPLE 1

Treatment of Acute Sinusitis

Uridine 5'-triphosphate (UTP) or $P^1,P^4$ di(uridine-5')-tetraphosphate ($U_2P_4$) is administered to patients diagnosed with acute sinusitis. UTP is administered via nasal drops or nasal spray, 2–3 times a day, for a total of 3–5 days during an acute episode of sinusitis. The concentration of UTP is in the range of $10^{-7}$ to $10^{-1}$ moles/liter (e.g., for UTP, 0.001 to 50 mg/mL). Treatment with UTP begins as soon as the presumptive diagnosis of sinusitis is made; not necessarily after antibiotic therapy is initiated. The length of treatment for each patient is one week (or as long as symptoms persist).

The effectiveness of UTP in promoting the drainage of blocked sinus fluid is measured by a decrease in symptomatic complaints as well as by the results of physical examinations.

The safety of UTP is assessed by standard safety measures of vital signs-heart rate, respiratory rate, blood pressure, electrocardiogram and laboratory blood tests (e.g., blood chemistries and complete blood count), as well as any adverse events observed/reported.

The subject methods and compounds described herein provide a means for inducing drainage of mucous secretions from the sinus passageways in a patient afflicted with sinusitis. The method comprises administering to the sinuses of the subject a uridine triphosphate such as uridine 5'-triphosphate (UTP), $U_2P_4$, or any analog of UTP in an amount effective to hydrate mucous secretions or stimulate ciliary beat frequency in the sinuses.

The invention now being fully described, it will be apparent to one of ordinary skill in the art that many changes and modifications can be made thereto without departing from the spirit or scope of the appended claims.

What is claimed is:

1. A method of treating sinusitis in a subject in need of such treatment, said method comprising:
    administering to the subject a compound of Formula I, or a pharmaceutically acceptable salt thereof, in a pharmaceutical carrier having an amount of said compound effective to promote fluid drainage from the sinuses:

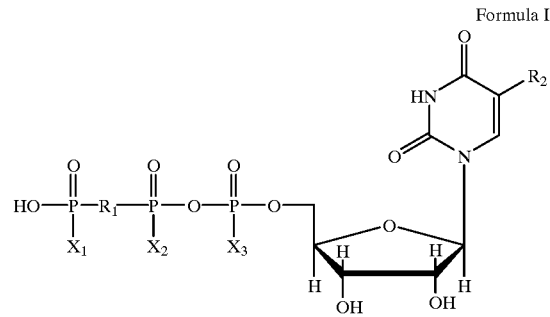

Formula I wherein:
    $X_1$, $X_2$, and $X_3$ are each independently selected from the group consisting of OH and SH;
    $R_1$ is selected from the group consisting of O, imido, methylene, and dihalomethylene; and
    $R_2$ is selected from the group consisting of H and Br.

2. A method according to claim 1, wherein said compound is delivered by administering a liquid/liquid suspension, including eye drops of said compound to the eyes, or nasal drops, powder or spray, of said compound to the nasopharngeal airways of said subject, such that a therapeutically effective amount of said compound contacts the sinuses of said subject either directly or via systemic absorption and circulation.

3. A method according to claim 1, wherein said compound is delivered by administering an oral form of said compound to the sinuses of said subject, such that a therapeutically effective amount of said compound contacts the sinuses of said subject via systemic absorption and circulation.

4. A method according to claim 1, wherein said compound is delivered by administering a nebulized aerosol suspension or solution of said compound to the nasopharyngeal airways of said subject, such that a therapeutically effective amount of said compound contacts the sinuses of said subject either directly or by systemic absorption and circulation.

5. A method according to claim 1, wherein said compound is delivered by administering a topical form of said compound to the sinuses via the nose, eyes, outer ear or nasopharyngeal airways of said subject, such that a therapeutically effective amount of said compound contacts the sinuses of said subject either directly or by systemic absorption and circulation.

6. A method according to claim 1, wherein said compound is delivered by administering an injected form of said compound, such that a therapeutically effective amount of said compound contacts the sinuses of said subject via systemic absorption and circulation.

7. A method according to claim 1, wherein said compound is delivered by administering a suppository form of said compound, such that a therapeutically effective amount of said compound contacts the sinuses of said subject via systemic absorption and circulation.

8. A method according to claim 1, wherein said compound is delivered by administering an intra-operative instillation of a gel, cream, powder, foam, crystals or liquid suspension form of the active compound such that a therapeutically effective amount of said compound contacts the sinuses either directly or via systemic absorption and circulation.

9. A method according to claim 1, wherein said compound is administered in an amount sufficient to achieve concentrations thereof on the surfaces of the sinuses of said subject of from about $10^{-7}$ to about $10^{-1}$ moles/liter.

10. A method according to claim 1, wherein $X_2$ and $X_3$ are OH.

11. A method according to claim 1, wherein $R_1$ is oxygen.

12. A method according to claim 1, wherein $R_2$ is H.

13. A method according to claim 1, wherein said compound of Formula I is selected from the group consisting of uridine 5'-triphosphate, uridine 5'-O-(3-thiotriphosphate), 5-bromo-uridine 5'-triphosphate and the pharmaceutically acceptable salt thereof.

* * * * *